United States Patent [19]

Heitmann et al.

[11] Patent Number: 4,941,482
[45] Date of Patent: * Jul. 17, 1990

[54] APPARATUS FOR MEASURING THE DENSITY OF A TOBACCO STREAM

[75] Inventors: Uwe Heitmann, Hamburg; Heinz-Christen Lorenzen, Wentorf; Wolfgang Siems, Hamburg; Peter Pinck, Gross-Hansdorf, all of Fed. Rep. of Germany

[73] Assignee: Körber AG, Hamburg, Fed. Rep. of Germany

[ * ] Notice: The portion of the term of this patent subsequent to Feb. 21, 2006 has been disclaimed.

[21] Appl. No.: 225,693

[22] Filed: Jul. 28, 1988

[30] Foreign Application Priority Data

Jul. 31, 1987 [DE] Fed. Rep. of Germany ....... 3725366

[51] Int. Cl.$^5$ ................................................ A24C 5/14
[52] U.S. Cl. ..................... 131/84.4; 131/905; 131/906
[58] Field of Search .................. 131/84.4, 905, 906, 131/908, 907

[56] References Cited

U.S. PATENT DOCUMENTS

| 3,056,026 | 9/1962 | Bigelow | 131/905 X |
| 3,146,780 | 9/1964 | Harrison et al. | 131/84.4 X |
| 3,334,240 | 8/1967 | Black | 131/907 X |
| 4,001,579 | 1/1977 | Lebet et al. | 250/233 |
| 4,350,170 | 9/1982 | Baier | 131/84.1 |
| 4,785,830 | 11/1988 | Moller et al. | 131/84.4 X |
| 4,805,641 | 2/1989 | Radzio et al. | 131/905 X |

FOREIGN PATENT DOCUMENTS

| 759532 | 10/1958 | United Kingdom | 131/280 |
| 1128003 | 9/1968 | United Kingdom | 131/906 |

Primary Examiner—V. Millin
Assistant Examiner—D. F. Crosby
Attorney, Agent, or Firm—Peter K. Kontler

[57] ABSTRACT

The density of a tobacco stream which is advanced by a foraminous conveyor toward the surplus removing station of a cigarette rod making machine is measured by one or more detectors each having one or more sources of infrared light and one or more photoelectric transducers. In order to avoid the generation of distorted signals in response to impingement of high-intensity radiation upon the transducer or transducers, each transducer is out of line with the path of direct propagation of radiation from the respective source or sources toward successive increments of the tobacco stream. The transducer or transducers receive infrared light which is scattered in and/or reflected by tobacco particles in the stream. Signals from the transducer or transducers are used to regulate the quantity of surplus which is removed from the stream.

4 Claims, 2 Drawing Sheets

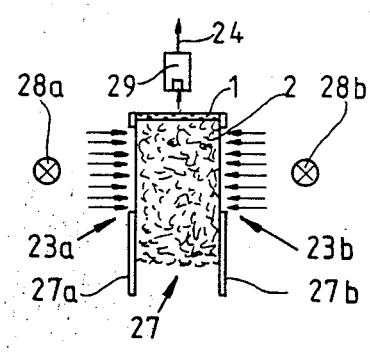
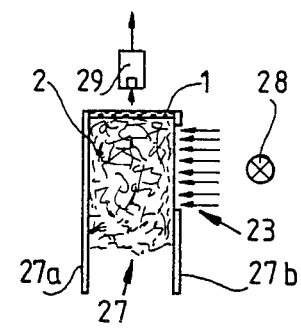
Fig. 2        Fig. 3
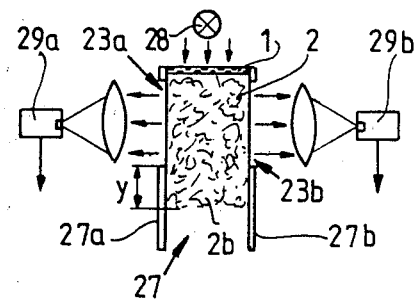
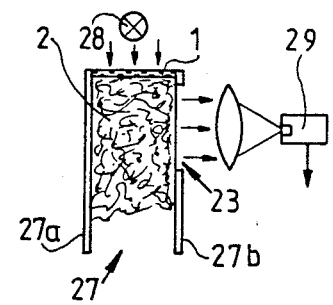
Fig. 4        Fig. 5
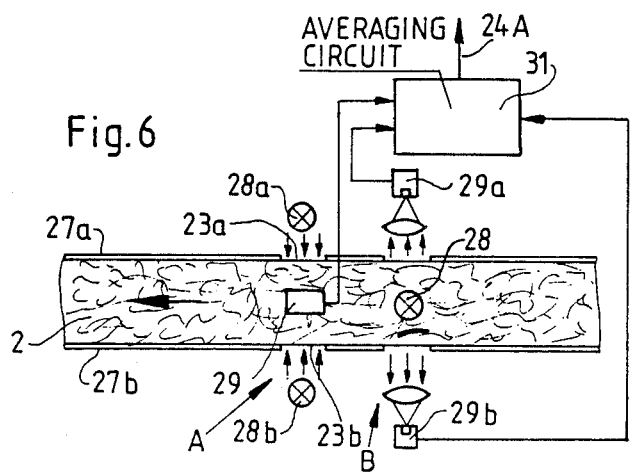
Fig. 6

APPARATUS FOR MEASURING THE DENSITY OF A TOBACCO STREAM

BACKGROUND OF THE INVENTION

The invention relates to improvements in apparatus for measuring the density of a tobacco stream, especially in a rod making machine. More particularly, the invention relates to improvements in apparatus which measure the density of successive increments of an advancing tobacco stream by causing one or more beams of radiation to penetrate into the stream and by ascertaining the characteristics (such as the intensity) of radiation which penetrates through the stream.

It is known to measure the density of a tobacco stream with a detector wherein a source of beta rays, visible rays or infrared rays directs one or more beams of radiation against the stream and a suitable transducer serves to generate signals which are indicative of the characteristics of that portion of each beam which has penetrated through the stream. Reference may be had, for example, to commonly owned copending patent applications Ser. Nos. 760,995 and 837,096 of Radzio et al. A drawback of presently known density measuring apparatus of the above outlined character is that the results of measurements are not reliable under any and all circumstances which are likely to be encountered in connection with the density measurement of a tobacco stream in a cigarette rod making or like machine. For example, if the stream exhibits pronounced hills and valleys, the intensity of radiation which penetrates through the stream is likely to reach a value which affects the accuracy of signals from the transducer of the detector. Thus, if the beam of radiation issuing from a source passes through the tobacco stream in a region where the stream exhibits a pronounced depression or valley, the intensity of radiation to which the transducer is exposed can reach a value which entails a distortion of the signal from the transducer to the evaluating circuit so that the signal is not truly indicative of actual density of the respective portion of the stream. The situation is aggravated if the stream of tobacco particles happens to be interrupted so that the entire beam of radiation issuing from the source impinges upon the transducer.

It was further discovered that heretofore known density measuring apparatus do not take into consideration certain other factors which are likely to adversely influence the accuracy of the measurement. For example, such conventional density measuring apparatus do not take into consideration the radiation scattering effect of tobacco particles which are located outside of the actual measuring or monitoring range of the detector, especially of tobacco particles which form the surplus and must be removed in order to convert the stream into a filler which is ready to be draped into a web of cigarette paper or other suitable wrapping material.

Still further, the quality of density measurement can be adversely influenced by localized accumulations of tobacco shreds and/or by fragments of tobacco ribs which find their way into the stream and advance past the density measuring station close to the locus of penetration of radiation into the stream. The transducer of the detector is likely to transmit an inaccurate signal (i.e., a signal which is not truly representative of the density of the corresponding increment of the stream) if the fragments of tobacco ribs and/or accumulations of tightly interlaced tobacco shreds interfere with predictable penetration of radiation through the advancing stream.

OBJECTS AND SUMMARY OF THE INVENTION

An object of the invention is to provide a novel and improved apparatus which can measure the density of successive increments of an advancing tobacco stream with a degree of accuracy much higher than that achievable with heretofore known apparatus.

Another object of the invention is to provide the apparatus with novel and improved means for preventing the generation and transmission of misleading signals when the stream exhibits pronounced hills and valleys.

A further object of the invention is to provide the apparatus with novel and improved means for preventing exposure of the signal generating component or components to excessive radiation.

An additional object of the invention is to provide the apparatus with novel and improved means for preventing fragments of tobacco ribs and/or unanticipated agglomerations of tobacco shreds from adversely influencing the measurement of density of the respective increments of the tobacco stream.

Still another object of the invention is to provide the apparatus with novel and improved means for compensating for the radiation scattering effect of those portions of the tobacco stream which are not in the immediate range of density monitoring instrumentalities.

A further object of the invention is to provide a novel and improved method of measuring the density of an advancing tobacco stream in such a way that unanticipated departures of the shape and/or density and or composition of certain increments of the stream from anticipated values do not adversely affect the measuring operation.

Another object of the invention is to provide a tobacco processing machine which embodies the above outlined apparatus.

An additional object of the invention is to provide novel and improved detector means for monitoring the density of successive increments of a tobacco stream which is on its way to the surplus removing station in a cigarette rod making or other tobacco processing machine.

A further object of the invention is to provide novel and improved tobacco guide means for use in the above outlined apparatus.

Another object of the invention is to provide the apparatus with novel and improved means for taking into consideration all known factors which adversely influence the measurements of density in conventional apparatus.

An additional object of the invention is to provide an apparatus which can be built into existing tobacco processing machines as a superior substitute for heretofore known density measuring apparatus.

SUMMARY OF THE INVENTION

One feature of the invention resides in the provision of an apparatus for measuring the density of a tobacco stream in a rod making machine. The apparatus comprises a first component including at least one radiation source which serves to direct radiation against the stream along a predetermined path whereby the extent of penetration of radiation through the stream denotes the density of the stream, and a second component including at least one radiation receiver (e.g., a photoelectric transducer) which serves to receive radiation that penetrates through the stream. In accordance with a feature of the invention, the radiation receiver is spaced apart from the path of radiation which issues from the source or sources so that the receiver is not exposed to radiation of excessive intensity if the tobacco stream is thinner than expected or the beam or beams of radiation do not encounter any tobacco. It can be said that the source or sources are disposed in a first plane and the receiver or receivers are disposed in a different second plane. The two planes are inclined relative to each other. This does not prevent the source or sources and the receiver or receivers from being located in a common plane which extends transversely of the stream.

In accordance with a presently preferred embodiment of the improved apparatus, the path is horizontal or substantially horizontal and the receiver or receivers are positioned to receive radiation which issues from the stream in a vertical or substantially vertical direction. Alternatively, the path can be vertical or substantially vertical, and the receiver or receivers are then positioned to receive radiation which issues from the stream in a horizontal or substantially horizontal direction.

The first component can include two radiation sources which serve to direct radiation along horizontal or nearly horizontal paths, and the means for advancing the stream can be designed to move the stream between the sources so that the radiation penetrates into opposite sides of the advancing stream. Alternatively, the second component can comprise two radiation receivers and the advancing means is then designed to move the stream between the two receivers so that the receivers receive radiation which issues from opposite sides of the advancing stream.

One of the first and second components can be disposed at a level above the stream.

The advancing means can comprise a conveyor which moves the stream in a predetermined direction. The apparatus can comprise a third component including at least one radiation source serving to direct radiation against the stream along a second predetermined path whereby the extent of radiation which penetrates through the stream is again indicative of the density of the stream, and a fourth component including at least one radiation receiver which serves to receive radiation issuing from the source of the third component and penetrates through the stream. The radiation receiver of the fourth component is spaced apart from the second path and the third and fourth components are located upstream of the first and second components (as considered in the direction of advancement of the stream) so that radiation which issues from the source of the first component penetrates through successive increments of the advancing stream downstream of the locus of penetration of radiation which issues from the source or sources of the third component.

The machine which embodies the improved apparatus is preferably provided with means for forming the stream with a surplus of tobacco and with means for removing the surplus from successive increments of the advancing stream.

The radiation which propagates itself from the stream toward the receiver or receivers of the second or fourth component advances along a further path which is inclined with reference to the corresponding predetermined path (of propagation of radiation from the source or sources of the first or third component). The apparatus or the machine in which the apparatus is installed further comprises a channel for the tobacco stream, and the channel has wall means with at least one window for radiation in one of the paths, i.e., in the path from a source to the stram or from the stream to a receiver. The window can include or constitute a diaphragm which permits penetration of a predetermined amount of radiation into the stream or issuance of radiation from a predetermined portion of each increment of the stream. The stream forming means is designed to deliver into the channel tobacco particles in such quantities that the stream contains the aforementioned surplus of tobacco, and such surplus is then removed by the surplus removing (called trimming or equalizing) means. The removal of surplus takes place downstream of the components of the improved apparatus, and the machine can comprise means for moving the surplus removing means between a plurality of levels to remove different quantities of surplus from the stream (the stream is normally caused to advance along a substantially horizontal path, i.e., along a path which is inclined to the vertical). The diaphragm is preferably located above the median level of the surplus removing means.

The means for advancing normally comprises (or can comprise) a foraminous conveyor which is located at a level above the stream (the conveyor can attract the stream to its underside by suction). One of the first and second and/or third and fourth components of the apparatus can be installed above the conveyor so that the radiation which propagates itself from or to such component above the conveyor must penetrate through the conveyor on its way toward or from the stream.

Each receiver has means for generating first signals which denote the ascertained density of successive increments of the tobacco stream and are transmitted to an evaluating circuit. The latter preferably further receives second signals from a density monitoring device which is designed to ascertain the density of successive increments of the stream in a substantially vertical plane The second signals influence the first signals to thus ensure that the signal which is generated by the evaluating circuit is truly repesentative of the density of successive increments of the stream.

In a presently preferred embodiment of the apparatus, each source is designed to emit infrared light.

Another feature of the invention resides in the provision of a method of measuring the density of a tobacco stream in a rod making machine. The method comprises the steps of advancing the stream along a first path, directing against the stream at least one beam of radiation along a second path adjacent a predetermined portion of the first path so that the radiation which propagates itself along the second path penetrates into the stream and that radiation which penetrates through successive increments of the stream is indicative of the density of the respective increments, and measuring the intensity of radiation which penetrates through the stream at a location which is out of line with the second path.

The novel features which are considered as characteristic of the invention are set forth in particular in the appended claims. The improved apparatus itself, however, both as to its construction and its mode of operation, together with additional features and advantages

BRIEF DESCRIPTION OF THE DRAWING

FIG. 2 is a fragmentary transverse vertical sectional view of the machine showing one embodiment of the density measuring apparatus with two radiation sources at the sides of and a radiation receiver above the tobacco stream;

FIG. 3 is a similar fragmentary transverse vertical sectional view but showing an apparatus with a single radiation source;

FIG. 4 is a similar fragmentary transverse vertical sectional view but showing a single radiation source at a level above and and two receivers at opposite sides of the tobacco stream;

FIG. 5 is a view similar to that of FIG. 4 but showing an apparatus with a single radiation receiver; and FIG. 6 is a fragmentary plan view of a twin apparatus with the radiation source of one unit and the radiation receiver of the other unit disposed at one side of the tobacco stream and the radiation receiver of the one unit and the radiation source of the other unit disposed at the other side of the stream.

DESCRIPTION OF PREFERRED EMBODIMENTS

Figure 1:
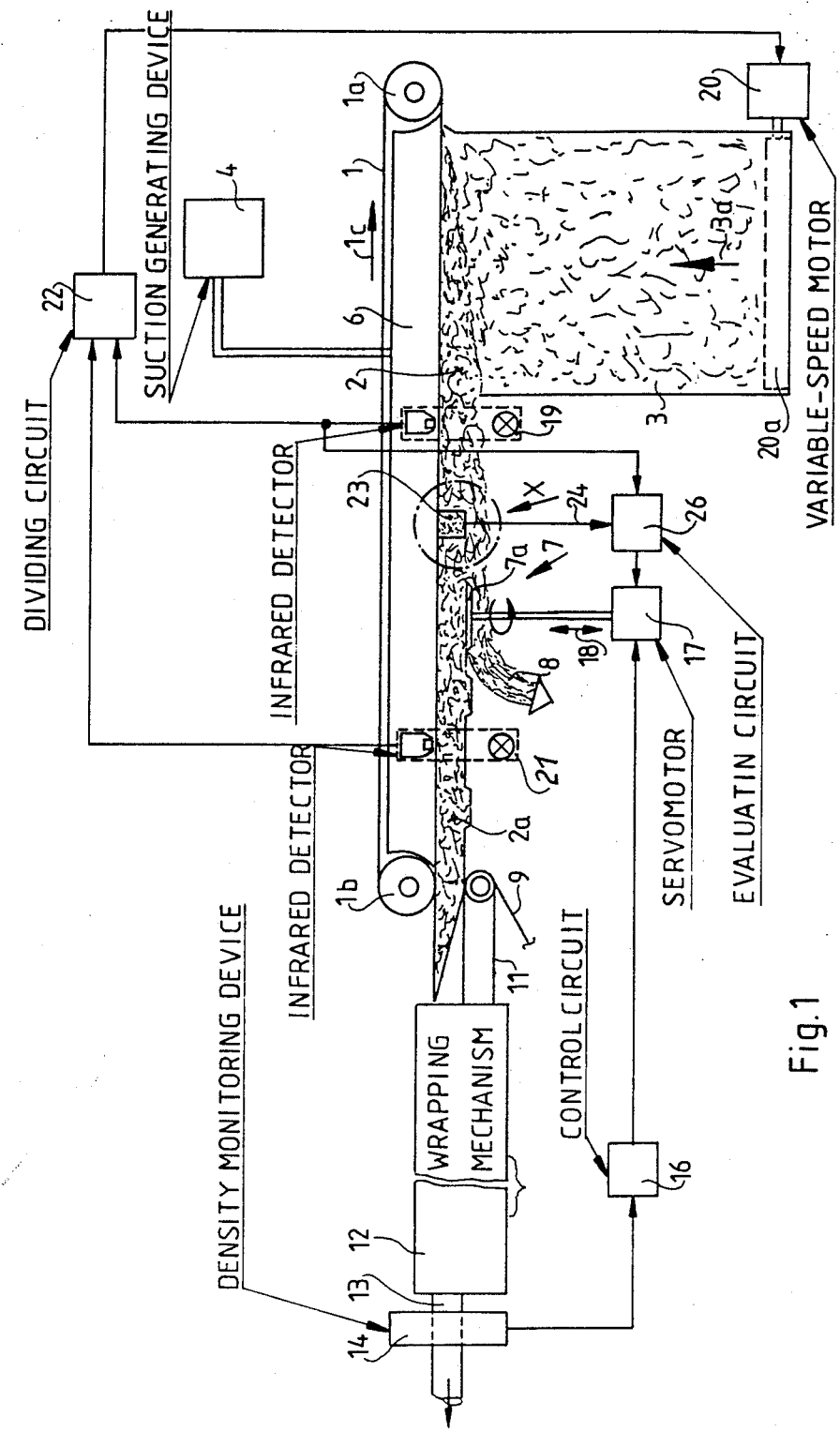
FIG. 1 is a fragmentary schematic partly elevational and partly vertical sectional view of a cigarette maker embodying a density measuring apparatus which is constructed and assembled in accordance with the present invention.

FIG. 1 shows a portion of a cigarette rod making machine wherein a continuous tobacco stream 2 is advanced by the lower reach of an endless foraminous belt conveyor 1 which is trained over pulleys 1a and 1b. The conveyor 1 is driven (by at least one of the pulleys 1a, 1b) in the direction of arrow 1c and the stream 2 is formed at the upper end of a duct 3 which serves to convey a rising shower of tobacco particles (such as shreds of tobacco leaf laminae) toward the underside of the lower reach of the conveyor 1 (note the arrow 3a). The lower reach of the conveyor 1 is adjacent the underside of a suction chamber 6 which has an outlet connected to a suction generating device 4 so as to ensure that the particles of tobacco which form the stream 2 are attracted to and advance with the conveyor 1 in the direction of arrow 1c. The duct 3 delivers particles of tobacco at such a rate that the stream 2 contains a surplus 8 of tobacco, i.e., more tobacco than is necessary to form a continuous filler 2a which is thereupon draped into a web 9 of cigarette paper or other suitable wrapping material. The web 9 is drawn off a reel (not shown) and is advanced by the upper reach of a second endless belt conveyor 11 (known as garniture) which causes the filler 2a and the web 9 to advance through a conventional wrapping mechanism 12 wherein the web is draped around the filler and the filler is compressed so as to constitute the core of a continuous cigarette rod 13. The latter is subdivided into sections of predetermined (unit or multiple unit) length, and such sections constitute discrete plain cigarettes or are supplied to a filter tipping machine to be assembled with filter rod sections.

The means for removing the surplus 8 from the fully grown tobacco stream 2 downstream of the duct 3 comprises a conventional trimming or equalizing device 7 having one or more rotary disc-shaped tobacco engaging and severing members 7a. The illustrated trimming device 7 is designed to provide the filler 2a with longitudinally spaced apart portions which contain more tobacco than the portions between them because the filler 2a is to be converted into the core of a cigarette rod 13 which is to yield plain cigarettes with so-called dense ends.

The disc-shaped severing member or members 7a of the trimming device 7 are movable up and down between a plurality of different levels (as indicated by the arrow 18), i.e., to positions at different distances from the lower reach of the conveyor 1, so as to change the quantity of tobacco which forms the removed surplus 8.

The rod making machine of FIG. I further comprises a nuclear density measuring device 14 which is located downstream of the wrapping mechanism 12 and monitors the density of successive increments of the core in the cigarette rod 13. The output of the density measuring device 14 transmits signals, which denote the density of successive increments of the condensed filler 2a, to a control circuit 16 of known design which, in turn, transmits signals to a servomotor 17 to move the disc-shaped member or members 7a of the trimming device 7 up or down and to thus change the density of the filler 2a. The monitoring device 14 and the control circuit 16 are standard components of many rod making machines and are manufactured and sold by the assignee of the present application.

The rod making machine of FIG. 1 also comprises conventional means for regulating the quantity of surplus 8 by changing the quantity of tobacco particles in the shower within the duct 3. Such regulating means comprises a first detector 19 upstream and a second detector 21 downstream of the trimming station (as seen in the direction of advancement of the stream 2). Each of the detectors 19, 21 comprises a source of infrared radiation at one side of the path for the stream 2 and filler 2a, and a suitable photoelectric transducer at the other side of such path opposite the respective radiation source. The outputs of the transducers transmit signals which are indicative of the mass of tobacco particles in the respective portions of the path for the stream 2 and filler 2a, and such signals are processed in a dividing circuit 22. The output of the dividing circuit 22 transmits signals to a variable-speed motor 20 for an impeller 20a which serves as a means for propelling particles of tobacco into the duct 3 at a rate which is a function of rotational speed of the impeller. The signal at the output of the circuit 22 is a quotient of signals which are transmitted by the transducers of the detectors 19 and 21. It will be noted that the path for the stream 2 and filler 2a is substantially horizontal and that the radiation sources of detectors 19, 21 emit beams of infrared light which are substantially vertical so that the beam of infrared light which is emitted by the radiation source of the detector 19 traverses the entire untrimmed stream 2 downstream of the duct 3 but upstream of the trimming station.

The improved density measuring apparatus of the rod making machine which is shown in FIG. 1 is located upstream of the trimming device 7 and is designed to monitor primarily the density of that (upper) portion of the stream 2 which is to form the filler 2a, i.e., which is to advance at a level above the severing member or members 7a of the trimming device 7. The density measuring apparatus can be constructed in a manner as shown in FIG. 2, 3, 4, 5 or 6; its location is indicated in FIG. 1 by a phantom-line circle A. Such apparatus comprises at least one window or diaphragm 23 which is located above the median level of the severing member or members 7a beneath the lower reach of the conveyor 1. The output 24 of the receiver or transducer of the apparatus at the locus A transmits signals which are indicative of the density of the upper portions of successive increments of the stream 2, and such signals are processed by an evaluating circuit 26 which further receives signals from the transducer of the detector 19. The evaluating circuit 26 has an output which can transmit signals to the motor 17 to influence the level of the severing member or members 7a as a function of monitored density of the stream 2 ahead of the trimming station. Adjustments of the trimming device 7 in response to signals from the evaluating circuit 26 serve to ensure that the quantity of tobacco shreds which are permitted to bypass the trimming device 7 is changed accordingly, i.e., that the density of the filler 2a in the cigarette rod 13 is changed.

FIG. 2 shows the untrimmed tobacco stream 2 in a transverse vertical sectional view. This stream is advanced in an inverted U-shaped channel 27 having two parallel walls 27a, 27b extending downwardly from the lower reach of the conveyor 1. The conveyor 1 constitutes the top wall of the channel 27 and each of the walls 27a, 27b is provided with a window-like diaphragm (23a, 23b) of predetermined area which is disposed above the average or median level of the severing member or members 7a (not shown in FIG. 2). The apparatus of FIG. 2 comprises a first component having two sources 28a, 28b of infrared light which direct beams of such light along substantially horizontal paths so that infrared radiation penetrates through the respective diaphragms 23a, 23b prior to entering successive increments of the stream 2 in the channel 27. The apparatus of FIG. 2 further comprises a second component including a receiver 29 of infrared light. The receiver 29 is or can constitute an optoelectric transducer having an output 24 which transmits signals denoting the density of successive increments of the stream 2 at the level of the diaphragms 23a, 23b. It will be noted that the transducer 29 is spaced apart from the path of propagation of radiation from the source 28a or 28b into the stream 2. This ensures that the transducer 29 is not overexposed to infrared light, e.g., if the underside of the stream 2 in the channel 27 is formed with highly pronounced hills and valleys so that, were the transducer 29 located at 28b, radiation from 28a could directly impinge upon the transducer with the result that the signal from the output 24 of the transducer would fail to accurately denote the monitored density of successive increments of those portions of the stream 2 which advance at the level between the diaphragms 23a and 23b. As can be seen in FIG. 2, radiation which issues from the sources 28a, 28b propagates itself primarily along horizontal paths, and radiation which issues from the stream 2 and passes through the lower reach of the conveyor 1 on its way toward the transducer 29 advances along a substantially vertical path. Otherwise stated, and referring to an imaginary simple rectangular coordinate system, radiation from the sources 28a, 28b propagates itself along the X-axis and radiation from the stream 2 toward the transducer 29 propagates itself along the Y-axis of the coordinate system.

FIG. 3 shows a modified apparatus wherein the first component includes a single radiation source 28 and the second component includes a single receiver or transducer 29. The latter is again located at a level above the lower reach of the conveyor 1 and the stream 2. The wall 27b of the channel 27 has a window-like diaphragm 23 for radiation which is emitted by the source 28. Such radiation must change the direction of its propagation before it can reach the transducer 29 because the latter is not in line with the path of propagation of infrared light from the source 28.

In the apparatus of FIG. 4, the first component comprises a single radiation source 28 at a level above the stream 2 in the channel 27, and the second component comprises two receivers or transducers 29a, 29b at opposite sides of the stream. These transducers receive radiation which issues from the stream 2 and passes through the respective diaphragms 23a, 23b in the walls 27a, 27b.

FIG. 5 shows a modification of the apparatus of FIG. 4. The first component again comprises a single radiation source 28 at a level above the lower reach of the conveyor 1, and the second component comprises a single receiver or transducer 29 which receives radiation issuing from the stream 2 and passing through a window-like diaphragm 23 in the wall 27b of the channel 27.

The operation of apparatus which are shown in FIGS. 2 to 5 is based on the so-called remission principle according to which the transducer or transducers receive radiation which is reflected by and/or scattered in successive increments of the stream 2. Such mode of operation ensures the generation of signals having a pronounced intensity. However, it has been found that the intensity of signals which are generated by the transducer 29 or by the transducers 29a, 29b are also influenced, or can be influenced, by radiation which is scattered in the region beneath the diaphragm or diaphragms in the wall or walls of the channel 27. Such region is indicated at y in FIG. 4. Therefore, signals which are generated and transmitted by the transducer or transducers of the improved apparatus are compared in the evaluating circuit 26 of FIG. 1 with signals from the transducer of the detector 19, i.e., from a detector which monitors the density of the entire stream 2 ahead of the trimming station, namely the density of the stream portion which is to constitute the filler 2a as well as the density of the portion 2b (FIG. 4) in the region y at a level beneath the respective diaphragms 23a and 23b.

An advantage which is shared by each of the apparatus shown in FIGS. 2 to 5 is that impingement of intense radiation upon the transducer 29 or transducers 29a, 29b is prevented by the simple expedient of installing the transducer or transducers out of line with the direction of propagation of infrared radiation from the source 28 or sources 28a, 28b toward the tobacco stream 2. Thus, the accuracy of signals which are transmitted by the output or outputs 24 of the transducer or transducers is not affected by eventual deep valleys in the underside of the stream 2 and/or by total absence of tobacco particles in the channel 27.

The improved apparatus can be designed in such a way that it is also much less likely to be adversely influenced by potential accumulations of tightly interlaced tobacco shreds and/or by the passage of fragments of tobacco ribs past the density monitoring station. Such accumulations of shreds and fragments of ribs could distort the signals at the output or outputs of the transducer or transducers, e.g., while passing very close to the locus of penetration of radiation from one or more sources of infrared light into the stream 2. The adverse influence of such accumulations and/or of fragments of tobacco ribs is reliably prevented if the improved apparatus is constructed in a manner as shown in FIG. 6. This apparatus comprises two units A and B which may but need not be identical and each of which can constitute an apparatus of the type shown in FIG. 2, 3, 4 or 5. The unit B is located upstream of the unit A, as considered in the direction of advancement of the stream 2 in the channel including the walls 27a and 27b. For example, the unit A can be constructed in a manner as shown in FIG. 2, and the unit B can be constructed in a manner as shown in FIG. 4. The outputs of the transducers of the units A and B transmit signals to an averaging circuit 31 which transmits an averaged output signal (at 24A) to the evaluating circuit 26 of FIG. 1. The first component (radiation sources 28a, 28b) of the unit A directs infrared light against opposite sides of the stream 2 in the channel including the walls 27a, 27b whereas the corresponding component (radiation sources 28) of the second unit B emits radiation vertically downwardly so that such radiation penetrates through the conveyor (not shown in FIG. 6) prior to entering the stream 2.

The averaging circuit 31 takes into consideration the mutual spacing of the units A and B, i.e., the fact that radiation which is emitted by the source 28 of the unit B penetrates into successive increments of the stream 2 before such increments reach the locus of the unit A and are penetrated into by radiation issuing from the sources 28a and 28b.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of measuring the density of an unwrapped tobacco stream in a rod making machine, comprising the steps of advancing the stream by a radiation-permeable conveyor along a first path; directing against the stream at least one beam of radiation along a second path adjacent a predetermined portion of said first path so that radiation which propagates itself along the second path penetrates into and through the stream and through the conveyor and that radiation which penetrates through successive increments of the stream is indicative of the density of the respective increments; and measuring the intensity of radiation which penetrates through and issues from the conveyor.

2. Apparatus for measuring the density of an unwrapped tobacco stream in a rod making machine, comprising means for advancing the stream in a predetermined direction; a first component including at least one radiation source arranged to direct radiation against the stream along a predetermined path whereby the extent of penetration of radiation through the stream is indicative of density of the stream; a second component including at least one radiation receiver positioned to receive radiation which penetrates through and issues from the stream, said radiation receiver being spaced apart from said path; a third component including at least one radiation source arranged to direct radiation against the stream along a second predetermined path whereby the extent of penetration of such radiation through the stream is indicative of density of the stream; and a fourth component including at least one radiation receiver arranged to receive radiation which issues from the source of said third component and penetrates through the stream, the radiation receiver of said fourth component being spaced apart from said second path and said third and fourth components being located upstream of said first and second components so that radiation issuing from the source of said first component penetrates through successive increments of the advancing stream after such increments advance into and beyond the range of the source of said third component.

3. Apparatus for measuring the density of an unwrapped tobacco stream in a rod making machine wherein the rod making machine comprises means for advancing the stream including a foraminous conveyor disposed at a level above the stream, said apparatus comprising a first component including at least one radiation source arranged to direct radiation against the stream along a predetermined path whereby the extent of penetration of radiation through the stream is indicative of density of the stream; and the second component including at least one radiation receiver positioned to receive radiation which penetrates through and issues from the stream, said radiation receiver being spaced apart from said path and one of said components being disposed above the conveyor so that radiation between the stream and said one component passes through the conveyor.

4. Apparatus for measuring the density of an unwrapped tobacco stream in a rod making machine wherein the rod making machine comprises a tobacco channel and means for advancing the stream in the channel, said apparatus comprising a first component adjacent the tobacco channel and including at least one radiation source arranged to direct radiation against the stream along a predetermined path whereby the extent of penetration of radiation through the stream is indicative of density of the stream; a second component including at least one radiation receiver adjacent the tobacco channel and positioned to receive radiation which penetrates through and issues from the stream, said radiation receiver being spaced apart from said path and including means for generating first signals having characteristics which are indicative of the intensity of radiation that has passed through the stream and reaches said receiver, the tobacco channel of the rod making machine having wall means provided with a window for radiation between the stream in the tobacco channel and one of said components, said window being positioned to transmit a portion of radiation which is influenced by tobacco at the level of the window and at a level below the window; means for evaluating said signals; and means for monitoring the density of successive increments of the stream in a substantially vertical plane including means for generating second signals denoting the density of successive increments of the stream in said plane and for transmitting said second signals to said evaluating means to influence said first signals.

* * * * *